united States Patent [19]

Barwale et al.

[11] Patent Number: 4,857,465
[45] Date of Patent: Aug. 15, 1989

[54] WHOLE PLANT REGENERATION VIA ORGANOGENESIS AND SOMACLONAL VARIATION IN GLYCINE SPECIES

[75] Inventors: Usha B. Barwale; Jack M. Widholm, both of Champaign, Ill.

[73] Assignee: Lubrizol Genetics, Inc., Wickliffe, Ohio

[21] Appl. No.: 936,812

[22] Filed: Dec. 2, 1986

[51] Int. Cl.$^4$ .............................................. C12N 5/00
[52] U.S. Cl. ........................... 435/240.49; 435/240.5; 435/240.54
[58] Field of Search ............ 435/240.4, 240.5, 240.54, 435/240.49; 800/1

[56] References Cited

PUBLICATIONS

Flick, C., 1983, pp. 393-404, In: Handbook of Plant Cell Culture, vol. 1, Evans et al., eds., Macmillan: New York.
Brevedan et al., 1978, Agron. J., 70(1):81-84.
Hu et al., 1983, p. 216, In: Handbook of Plant Cell Culture, vol. 1, Evans et al., eds., Macmillan: New York.
Davidonis et al., 1983, Plant Sci. Lett. 32:89-93.
Grant, J., 1984, Plant Cell Tissue Organ Culture, 3:169-173.
Hisajima et al., 1986, Plant Physiol, 67 (Suppl 4):28.
Evans et al., 1981, pp. 89-95, In: Plant Tissue Culture: Methods and Applications in Agriculture, Academic: New York.
Hildebrand et al. (1986), Biotechnology in Agriculture and Forestry (Springer-Verlag, Berlin Heidlberg, Y.P.S. Baja, ed.), 2:283-308.
Kartha et al. (1981), Can. J. Bot., 59:1671-1679.
Kameya et al. (1981), Plant Science Letters, 21:289-294.
Cheng et al. (1980), Plant Sci. Lett., 19:91-99.
Saka et al. (1980), Plant Sci. Lett., 19:193-201.
Widholm et al. (1983), Plant Cell Rep., 2:19-20.
Beversdorf et al. (1977), Crop Sci., 17:307-311.
Newell et al. (1985), Plant Cell Tuss. Organ Culture, 4:145-149.
Barwale (1986), Master Thesis, "Screening of Soybean Cultivars for Plant Regeneration Potential & Regeneration of Soybean Plants from Undifferentiated Tissue."
Barwale et al. (1986), Theor. Appl. Genet., 72:423-428.
Kerns et al. (1986), Plant Cell Rep., 5:140-143.
Barwale et al. (1986), Planta, 167:473-481.
Miller (1985), Science News, 128:120-121.

*Primary Examiner*—Charles F. Warren
*Assistant Examiner*—David T. Fox
*Attorney, Agent, or Firm*—Greenlee and Associates

[57] ABSTRACT

A method is provided for the production of organogenic tissue culture and regeneration of whole plants of Glycine species, preferably *Glycine max*, involving the use of an organogenic culture medium comprising high cytokinin, preferably at least about 10 $\mu$M BAP, and also preferably comprising at least about 6 times normal concentration of MS micronutrients. The organogenic culture medium is useful for the production of plants embodying desirable characteristics induced by somaclonal variation.

11 Claims, No Drawings

WHOLE PLANT REGENERATION VIA ORGANOGENESIS AND SOMACLONAL VARIATION IN GLYCINE SPECIES

FIELD OF THE INVENTION

This invention relates to an organogenic method of regenerating whole plants from in vitro tissue cultures of soybean and other Glycine species, and to the induction of somaclonal variation in said species.

BACKGROUND OF THE INVENTION

A method for achieving regeneration of soybean and its relatives from tissue culture has long been sought. Unlike such easily regenerable species as tobacco and petunia, soybean has been resistant to many prior attempts to regenerate whole plants from tissue culture. Tissue cultures are very desirable in allowing the induction of desirable traits into soybean or species capable of breeding therewith (such as *G. soja*) via somaclonal variation. They would also be of benefit to genetic engineers in allowing transformtion of cells by infection with Agrobacteria or by other means resulting in transformed cells in culture containing foreign DNA which could then be regenerated into whole plants bearing seed and expressing foreign genes.

D. A. Evans, et al. (eds.) (1983) in *Handbook of Plant Cell Culture*, vol. 1, at pp. 178–179, discuss the three possible routes available for in vitro propagule multiplication of plants in general: (a) enhanced release of axillary buds; (b) production of adventitious shoots through organogenesis; and (c) somatic embryogenesis.

Axillary bud proliferation from meristem, shoot tip, or bud cultures as a means of regeneration involves the use of an incipient shoot that has already been differentiated in vivo. Thus, to establish a complete plant, only elongation and root differentiation are required. In vitro organogenesis and embryogenesis, on the other hand, involve developmental changes: usually the formation of callus with subsequent reorganization into plantlets. This has not been easy to achieve in most plants. Evans, et al. supra at p. 178 discuss the failure of prior organogenic methods in soybean, stating that "induction of axillary bud proliferation seems to be applicable in many cases; e.g., carnation and soybean, where methods of organogenesis and embryogenesis fail."

They go on, at pp. 178–79, to state: "Although the rate of plantlet multiplication by means of organogenesis and embryogenesis is astonishing, their regeneration capacity usually diminishes rapidly after a number of subcultures, and eventually this morphogenic potential is completely lost. The initial multiplication rate for axillary bud proliferation, on the other hand, is rather slow. The rate, nevertheless, increases during the first few subcultures and eventually reaches a steady plateau during subsequent subculture cycles." These authors thus recommend axillary bud proliferation as opposed to organogenesis and embryogenesis for commercial production.

Such a bud proliferation method is described by M. S. Wright, et al., (1986) in "Plant Regeneration by Organogenesis in *Glycine max*", Plant Cell Reports, 5: 150–154. This method involves the germination of seeds of *Glycine max* (L.) on MS medium (Murashige, T. and Skoog, F. (1962) Physiol. Plant. 15: 473) containing half the recommended concentration of inorganic salts and 5 $\mu$M BA (benzyladenine) also known as BAP (benzylaminopurine), CAS Registry No. 1214-39-7. Cotyledonary nodes were excised from the germinated seedlings, and non-nodal tissue removed. The piece of nodal tissue was cultured on the germination medium, then transferred to the same medium altered to contain only one fourth the recommended concentration of organic salts and 5 $\mu$M BA. The nodes were subsequently subdivided and transferred to further media, and finally to soil-containing media for whole plant maturation. This method appears to be a meristemic propagation method, not going through a stage of de-differentiated cells. The article states that specific superficial regions of the cotyledonary node of soybean can be induced to become meristematic and initiate shoots, and that the constant presence of BA during culture maintains shoot morphogenesis from proregenerative tissue.

Few methods for regenerating Glycine subgenus soja, comprising *G. max* (soybean) and *G. soja* from tissue culture have been developed, although greater success has been achieved with wild relatives such as *G. canescens* and *G. clandestina*.

D. F. Hildebrand, et al., (1986), in a review article, "Soybean [*Glycine max* (L.) Merr.]," Biotechnology in Agriculture and Forestry Vol. 2: Crops I (Y. P. S. Bajaj, ed.) 283–308, (Table 4) summarizes recent in vitro regeneration work on Glycine, and at 293 cites the references discussed below under the heading "Meristem Culture."

K. K. Kartha, et al. (1981) "Plant Regeneration from meristems of grain legumes: soybean, cowpea, peanut, chickpea and bean," Can. J. Bot. 59: 1671–1679, describe plant regeneration from shoot apical meristems of soybean on a medium containing 1 $\mu$M NAA and 0.05–0.1 $\mu$MBA. Whole plants were regenerated. Under higher concentration for BA, callus was formed but whole plant regeneration was not achieved.

T. Kameya, et al. (1981), "Plant Regeneration from Hypocotyl Sections of Glycine Species," Plant Sci. Lett. 21: 289–294, disclose the use of hypocotyl sections from seedling *G. canescens* and *G. tomentella*, cultured on MS medium supplemented with NAA and BA at various concentrations to regenerate normal plants. From the eight species tested including *G. max* and *G. soja*, regeneration of shoots at high frequency was observed only from hypocotyl sections of *G. canescens* using 1–5 mg/l (5–25 $\mu$M) BA.

T. Y. Cheng, et al. (1980), "Plant Regeneration from Soybean Cotyledonary Node Segments in Culture," Plant Sci. Lett. 19: 91–99, report the stimulation of multiple shoot-bud formation of soybeans in culture using conditioned cotyledonary node segments from seedlings. The medium used contained 0.25 $\mu$M of the auxin IBA (indole butyric acid) and 5–50 $\mu$M BAP. This method did not involve the formation of callus, but rather the use of explants. Concentrations of BAP higher than 10 $\mu$M inhibited the development of main shoots and roots, and shoot buds formed at the cotyledonary node region. It is not clearly reported that whole plants capable of independent growth in soil were regenerated.

H. Saka, et al. (1980), "Stimulation of Multiple Shoot Formation of Soybean Stem Nodes in Culture," Plant Sci. Lett. 19: 193–201, similarly describe the formation of shoot-buds on stem nodes or apices of *G. max* using a culture medium containing the auxin IBA and 5–50 $\mu$M BAP. Callus formation was reported which interfered with shoot bud formation. Neither emergence of new meristems from callus tissue nor whole plant regeneration were reported.

None of the foregoing references describe an organogenic regeneration method in which a tissue culture capable of producing new meristemic centers can be maintained.

In addition to the foregoing references cited in the Hildebrand, et al. review article, the following are illustrative of the state of the art.

J. M. Widholm, et al. (1983), "Shoot Regeneration from *Glycine canescens* Tissue Cultures," Plant Cell Reports 2: 19–20, report shoot induction from calli obtained from cotyledons and hypocotyls of *G. canescens* using several media including media containing NAA and 5 mg/l (25 µM) BAP. Whole plants were not regenerated, and root formation was infrequent.

W. D. Beversdorf, et al., in "Degrees of Differentiation Obtained in Tissue Cultures of Glycine Species," (1977) Crop Sci. 17: 307–311, reported obtaining compact nodules of meristem-like cells which they called "growth centers." Using an induction medium containing 2,4-D (2,4-dichlorophenoxyacetic acid) and/or NAA (alpha-napthaleneacetic acid) with 0.5 mg/l kinetin (6-furylaminopurine) to culture hypocotyl sections of *G. max* and *G. soja*, Beversdorf, et al. achieved "growth centers," but no further development into plantlets.

C. A. Newell, et al. (1985) "Protoplast culture and plant regeneration in *Glycine canescens*," Plant Cell Tissue Organ Culture 4: 145–149 describe the regeneration of whole plants of *G. canescens* from protoplasts taken from seedling hypocotyl tissue. The shoot-inducing medium contained BA at 0.4 mg/l (2 µM) and NAA at 0.1 and 1.0 mg/l in some experiments reported.

None of the foregoing describe the culturing of immature embryos including *G. max* embryos in a medium containing high BAP or other cytokinin to obtain organogenic regeneration of whole plants.

Recent works by the inventors hereof are:

Master's Thesis by Usha B. Barwale, "Screening of Soybean Cultivars for Plant Regeneration Potential and Regeneration of Soybean Plants from Undifferentiated Tissue," cataloged by the University of Illinois Library Mar. 16, 1986. This thesis defines the organogenic medium used in this invention and the development of plants therefrom.

U. B. Barwale, et al. (1986) in "Screening of *Glycine max* and *Glycine soja* Genotypes for Multiple Shoot Formation at the Cotyledonary Node," Theor. Appl. Genet. 72: 423–428, described the germination of seeds of 178 genotypes in a B5 medium comprising 1 or 5 µm BAP, and counted the number of shoots formed at the cotyledonary node.

H. R. Kerns, et al. (1986), "Correlation of cotyledonary node shoot proliferation and somatic embryoid development in suspension cultures of soybean (*Glycine max* L. Merr.)", Plant Cell Reports 5: 140–143 disclose the induction of embryos on tissue derived from hypocotyl and cotyledon tissues from germinated seeds using a suspension medium not containing a cytokinin. Embryo formation appeared to correspond with the number of shoots formed at the cotyledonary node in the previous study. No regeneration of the embryos into whole plants was reported.

U. B. Barwale, et al. (1986), "Plant regeneration from callus cultures of several soybean genotypes via embryogenesis and organogenesis," Planta 167: 473–481, report much of the work upon which this patent application is based.

A recent commonly-assigned patent application relating to a different method of Glycine regeneration was filed Aug. 4, 1986, as U.S. patent application No. 893,256 of Glenn B. Collins, et al. This application describes a method for regeneration of *G. max* and other Glycine species via somatic embryogenesis involving the culturing of cotyledon tissue excised from immature embryos. That application does not disclose or claim the culturing of whole embryos in a medium containing high cytokinin to obtain organogenic regeneration.

SUMMARY OF THE INVENTION

This invention provides a highly efficient organogenic regeneration method for Glycine species, including *Glycine max* (soybean) through a sufficiently de-differentiated culture to allow the development of plants with desired characteristics via somaclonal variation. The method is effective with all soybean genotypes tested (54). Soybean is known to be the most difficult Glycine species to regenerate. The organogenic method of the invention is also useful for transformation and cell selection for desirable traits, suspension culture and protoplast production. This method is substantially more efficient than previous somatic embryogenesis regeneration methods.

This invention involves the culturing of immature embryos on an organogenic medium to form an organogenic tissue culture. The medium contains a cytokinin, preferably BAP, at a concentration sufficiently high to prevent germination of the embryo and promote organogenic shoot production, preferably at least about 10 µM, and more preferably between about 13 µM and about 14 µM, and preferably no more than about 15 µM.

The organogenesis medium may be any shooting medium known to the art, and is preferably an MS medium. The medium must contain a concentration of micronutrients sufficient to promote organogenic shoot production rather than embryo germination, preferably at least about 3 times normal concentration, and more preferably about 4 to 6 times normal concentration.

The immature embryo size is between about 1.5 mm and about 10 mm long, and preferably between about 4 and about 6 mm long when placed on the culture medium.

The culture is transferred to fresh medium periodically, preferably about every 2–3 weeks, and may be kept growing continuously so as to allow for somaclonal variation.

Somaclonal variation may occur spontaneously, or as a result of the application of selection pressure to a culture. The organogenic cultures described herein may be used to induce somaclonal variation; or embryogenic cultures as known to the art and described, e.g.; in U.S. patent application No. 893,256 or U. B. Barwale, et al. (1986), Planta, supra, maybe used. Examples of useful mutations produced by somaclonal variation are those conferring phenotypes having male sterility, twin seeds, amino acid overproduction, disease resistance, herbicide tolerance, stress tolerance, e.g. heat and cold resistance, ability to tolerate adverse soil conditions such as the presence of toxic metals, and maturity variations such as early maturity.

Variant phenotypes may be observed at the tissue culture level, the regenerant ($R_0$) level, the level of the progeny of the $R_0$ generation ($R_1$) or subsequent progeny levels resulting from selfing or back crossing parental and grandparental plants. Preferably, variants are observed in two or more progeny generations to ensure stable heritability.

To regenerate whole plants from the callus culture, shoots proliferating on the culture are subdivided and placed on regeneration media as is known to the art and grown in light, preferably a 16 hour photoperiod, to a height suitable for transfer to a rooting medium, preferably about 1 cm. After growing on hormone-free rooting media, preferably MS media, the plants may be transferred to soil-containing media for maturing.

Preferably, prior to transfer to the soil-containing media, the plants are transferred to a hydroponic medium, preferably comprising about ¼ strength Hoagland's solution containing special micronutrients. Plant viability and ability to set seed is greatly enhanced through the use of this hydroponic medium.

At a suitable height, preferably about 3 inches, plants are transferred to a soil-containing medium, and preferably are fertilized with a solution containing ionic nickel.

The plants to be regenerated from the organogenic callus by the foregoing methods may be chosen for variant or non-variant phenotypes.

As used herein, the term "organogenesis" and "organogenic culture" refer to the production of shoots in vitro from callus cell culture. An organogenic culture does not produce somatic embryos prior to shoot formation as does an embryogenic culture, nor does it involve the propagation of structures formed in vivo, as do axially bud proliferation or methods for cloning other types of plant structures.

Glycine species are species of the genus Glycine, including *G. max* and *G. soja*, as well as wild species such as *G. argyrea, G. canescens, G. clandestina, G. cyrtoloba, G. falcata, G. latifolia, G. latrobeana, G. tabacina,* and *G. tomentella*.

Somaclonal variation is a technique that takes advantage of spontaneous genetic changes that occur in plant cells in laboratory tissue culture to produce desirable phenotypes. A useful discussion of somaclonal variation is given in J. A. Miller (1985) "Somaclonal Variation," Science News 128: 120–121, incorporated herein by reference.

DETAILED DESCRIPTION OF THE PREFERRED EMBODIMENTS

Immature embryos from a Glycine species, preferably of sub-genus soja, and more preferably, of *Glycine max*, are cultured to regenerate whole plants via organogenesis. The immature embryos range in size from about 1.5 to about 10 mm, more preferably from about 4 to about 6 mm. The embryos must include the embryonic axis. It has been demonstrated that when the axis is dissected away, satisfactory organogenesis does not occur.

The immature embryos are plated on a culture medium. A number of suitable culture media are known to the art, including B5, L2, and MS medium (T. Murashige, et al. (1962) supra). The MS medium is preferred. It is important that the medium have a high cytokinin concentration. A number of cytokinins are known to the art, including BAP (6-benzylaminopurine, also called BA for benzyladenine), ADE (adenine sulfate), zeatin, kinetin, and 2-ip (2-iso pentanyladenine). Preferably the cytokinin is BAP. The cytokinin concentration should be sufficient to prevent germination of the embryo, preferably at least about 10 $\mu$M, and more preferably between about 13 and about 14 $\mu$M. The cytokinin concentration should not be so high as to kill the embryo, and preferably is not higher than about 15 $\mu$M.

The medium also preferably contains an auxin. Auxins known to the art may be used, for example NAA ($\alpha$-napthalene acetic acid), IAA (indole-3-acetic acid), IBA (indole-3-butyric acid), all the foregoing being similar to NAA; or 2,4-D (2,4-dichlorophenoxyacetic acid), picloram (4-amino-3,5,6-trichloropicolinic acid), pCPA (parachlorophenoxyacetic acid), 2,4,5-T (2,4,5-trichlorophenoxyacetic acid), and dicamba (2-methoxy, 3,6-dichloro-o-anisic acid), all the latter being similar to 2,4-D. Preferably an auxin similar to NAA is used, and most preferably NAA. The concentration of auxin should be sufficient to stimulate growth, and preferably, when the auxin is NAA, the concentration should be between about 0.1 and 0.4 $\mu$M, and preferably about 0.2 $\mu$M.

Additional components of the organogenesis medium may include thiamine preferably in an amount between about 0.5 and 5.9 $\mu$M, and more preferably about 5.0 $\mu$M, and proline, preferably in an amount between about 6 and about 24 mM, and more preferably about 12 mM. These components are not necessary for most genotypes, including A3127 and Williams 82, but may enhance growth of some genotypes.

Additionally, it has been found that increasing the concentration of the MS micro-elements to at least about 3 times normal concentration, and preferably from about 4 to about 6 times normal concentration increases organogenesis efficiency. The minor elements are $H_3BO_3$, $MnSO_4$, $ZnSO_4$, $KI$, $Na_2MoO_4$, $CuSO_4$ and $CoCl_2$. At lower concentrations of minor elements, about 2 times normal or less, the embryos germinate rather than forming organogenic callus. The most preferred forms and concentrations of minor elements are set forth in Table 1b.

The organogenic cultures are initially incubated in the dark at about room temperature for about 4 weeks, until shoots of a size suitable for transfer have formed.

The shoots are then transferred to regeneration media known to the art, preferably MSR media or R5 media as shown in Table 1a. As is known to the art, many suitable media for proliferation of shoots exist, however, the cytokinin concentration should be reviewed so as not cause formation of friable, non-organogenic callus. Preferably when the cytokinin used is BAP, the concentration on the regeneration medium is less than about 10 $\mu$M. The cultures should be grown in light on the regeneration medium, preferably cool-white fluorescent light at approximately 80 $\mu$M protons per square meter per second for about 16 hours at about room temperature (about 25° C.–28° C.) during the day and at reduced temperature during the night, preferably about 18° C.

The regeneration medium does not require high concentrations of minor elements or micronutrients as used in the organogenesis medium, and preferably has the formulation shown in Table 1a for MSR medium or R5 medium.

The organogenic cultures are preferably transferred from the regeneration medium every 2 or 3 weeks to fresh regeneration media until they reach the height of about 1 cm. At this point they are transferred to a rooting medium known to the art. Preferably this rooting medium is MS medium without growth regulators.

To minimize stress on the plants, following rooting, the plants may be transferred to a hydroponic medium, preferably comprising about ¼ strength Hoagland's solution (Hoagland, D. R., et al. (1950) "The water-culture method for growing plants without soil," California Agric. Exp. Sta. Bull. No. 347. The Hoagland's solution is preferably modified by the addition of a micronutrient solution containing KCl, $H_3BO_3$, $MnSO_4$, $ZnSO_4$, $CuSO_4$ and $(NH_4)_6Mo_7O_{24}$, preferably in the forms and at the concentrations shown in Example 1 (see Table 2). Preferably the hydroponic medium also contains an iron salt, preferably Fe 330 (Sequestrine 330 Fe, Ciba-Geigy), and is at a pH of about 6.5. When the hydroponic growth stage is omitted, regenerated plants rarely bear more than about 5 seeds per plant; using the hydroponic medium, plants generally bear at least about 10 seeds per plant up to about 100 seeds per plant. The survival rate in soil is also better, being about 80% after hydroponic growth as opposed to about 20% when this step is omitted. The plants are maintained in the hyroponic medium until they are large enough to transfer to soil without harm, preferably until they are about 3 inches tall, usually after about 7 to about 15 days.

Following the hydroponic growth, plants are transplanted to a medium comprising soil, preferably a mixture of 1:1:1 peat moss:vermiculite:soil. A fertilizer solution comprising ionic nickel is preferably used to fertilize plants growing in soil. The preferred fertilizer solution is described in Example 1 (see Table 3).

The organogenic tissue culture may be continuously maintained, transferring to fresh medium every 2 to 3 weeks, and about 10 about 40 plants may be regenerated upon every transfer, as each callus can be subdivided in about 4 to 6 pieces. The callus continually forms meristematic sites and puts out shoots.

The degree of mutation of plants regnerated from this callus material (see Example 2) is indicative of a high degree of de-differentiation in the callus, as is the fact that meristemic centers in different planes are observed.

The high incidence of variant phenotypes which occurs in plants regenerated from the organogenic cultures makes them useful for the induction of somaclonal variation. To induce somaclonal variation using the organogenic culture material, selection pressures may be applied to the callus culture. For example, herbicides such as glyphosate, paraquat and atrazine may be applied to the cultures at completely toxic or sublethal levels to induce resistant callus capable of producing plants carrying the resistance. Mutations producing paraquat tolerance by increasing levels of enzymes such as superoxide dismutase whose presence imparts disease resistance are doubly valuable. Atrazine resistance is valuable to lessen herbicide carryover damage even where the use of this compound directly on the crop is not contemplated.

Heat, e.g. about 40° C., and cold, e.g. about 4° C., treatments may also be applied for varying lengths of time to obtain heat and cold-resistant callus, which is preferably retested prior to plant regeneration.

Proline levels are known to accumulate during many stress conditions, and proline has been shown to enhance tolerance to some stresses. This selection for mutations with enhanced proline levels may be carried out, e.g. by selecting for resistance to toxic proline analogs, such as hydroxyproline or azetidine-2-carboxylate.

Amino acid selection can also be carried out to increase seed levels of the amino acids, e.g. of methionine by selection with a toxic methionine analog such as ethionine, or of tryptophan by selection with a toxic analog such as 5-methyltryptophan. Selection with a toxic phenylalanine analog may also be done to cause polyphenolic overproduction associated with insect and disease resistance.

Other useful selections include those for resistance to toxic soil conditions such as the presence of toxic heavy metals, e.g. cadmium, copper, zinc, and lead, as well as the presence of sodium chloride or low pH.

Selection for disease resistance, e.g. brown stem rot, preferably using culture filtrates of the causative organisms may also be carried out to produce resistant lines.

Other useful traits which may be induced by somaclonal variation include male sterility and developmental characteristics such as early maturity.

Alternatively, and as illustrated herein, many mutations occur without the application of special selection pressure. These include such desirable characteristics as male sterility, early maturity and twin seeds. After mutation induction, the stability of the induced phenotypes should be determined. Regenerated plants (the $R_0$ generation) are selfed to form an $R_1$ generation. This generation is then selfed to form an $R_2$ generation, which may be selfed to form an $R_3$ generation. $R_0$ plants do not exhibit any of the desired characteristics since they are mostly heterozygous and the traits seen are recessive for the most part. Desirable characteristics observed in the $R_1$ generation are followed in the $R_2$ and preferably the $R_3$ generation or a backcross of the $R_2$ and $R_1$ generations, and their segregation patterns observed. Additional selfed, backcrossed or hybrid generations may be required to show the desired degree of stability of the desired characteristic. Statistical analyses as known to the art are performed to determine such stable inheritance. Individuals showing stable inheritance are selected for further use in breeding programs.

The following examples are provided by way of illustration and not by way of limitation of this invention.

EXAMPLES

Example 1: Soybean Regeneration via Organogenesis

Soybean seeds were obtained from the U.S. Department of Agriculture Soybean Germplasm Collection at Urbana unless otherwise noted, and were grown in the field or the greenhouse. The genotypes used in this study were chosen based on a multiple-shoot-formation assay at the cotyledonary node (Barwale et al. (1986), Theor. Appl. Genet. supra.

| High Shoot producers (eight or more shoots): | | |
|---|---|---|
| Ada | PI 30.692 | PI 79.739 |
| Blackhawk | PI 31.122 | PI 404.155A |
| Carlin | P I36.653 | Sooty |
| Intermediate shoot producers (six to eight shoots): | | |
| Adams | J-88 | PI 53.650A |
| Capitol | J-103 | Wayne |
| Century | J-105 | Wells |
| Earlyana | Mitchell | Wisconsin Black |
| Habaro | PI 153.292 | |
| Henry | PI 227.327 | |
| Lines not tested in the multiple-shoot assay: | | |
| Birch and Oak | J-122 | Simpson |
| CN 290 | LN 80-16017 | Sparks |
| CN 210 | PI 86.063 | Williams 79 |
| 33D | Pixie | Williams 82 |
| Harsoy | Sherman | |

(All J lines were obtained from the Jacques Seed Co., Prescott, Wis., USA; A3127 from Asgrow Seed Co., KAlamazoo, Mich., USA; Birch and Oak from Illinois Foundation Seeds, Tolono, Ill., USA; 33D from Dr. J. Harper, University of Illinois, Urbana.)

Embryos ranging in size from 0.5 to 10 mm were excised from pods which had been self-sterilized in 0.78% NaOCl, prepared from a commercial bleach with a drop of Tween 80 (polyethylene sorbitan monooleate; Nutritional Biochemicals, Cleveland, Ohio, USA), for 25–30 minutes and subsequently rinsed in sterile deionized distilled water twice for at least 5 minutes each time. The embryos were removed by taking the seed coat off the ovules by cutting next to the hilum which insured an intact embryo. These embryos were placed on the organogenesis (OR) medium (Table 1a) and incubated in the dark at $25\pm2°$ C. for four weeks. When EB medium was used somatic embryos formed rather than shoots. Shoots formed on OR medium were transferred to regeneration media MSR and R5 (Table 1a) at 25° C. during the day (light from cool-white fluorescent lamps, Sylvania, Fall River, Mass., USA; approx. 80 $\mu$mol photons $m^{-2}s^{-1}$ for 16 h) and 18° C. at night. The organogenic cultures were transferred every two or three weeks and maintained on MSR and R5 medium at 16 hour photoperiod with changing day and night temperature. After the shoots had reached a height of about 1 cm they were transferred to tubes containing hormone-free MS medium (Murashige and Skoog (1962) supra) for rooting. Following rooting the plants were usually transplanted in the greenhouse in 0.25 strength Hoagland's solution No. 1 (Hoagland, D. R., et al. (1950) supra) in 1-liter canning jars covered with aluminum foil, and aerated continuously. Two holes about 1 cm in diameter were made in the lid and the plants held in these with a sponge, with their roots immersed in the liquid.

The Hoagland's solution was modified by the addition per liter of Hoagland's solution of 4 ml of a micronutrient solution as shown in Table 2, and 2 ml of a 9.5 g/l solution of Fe 330. The solution was at a pH of 6.5.

TABLE 1a

Composition of media used in these experiments; all were solidified using 6g $1^{-1}$ Bacto-agar[a]

| Medium | Composition |
|---|---|
| OR | MS major salts + 4X concn. of minor elements[b] + B5 vitamins[c] + 13.3 $\mu$M BAP[d] + 0.2 $\mu$M NAA[d] + 5.0 $\mu$M thiamine[d] + 12 mM proline[d] |
| EB | MS basal medium + 43.0 $\mu$M NAA + 5.0 $\mu$M thiamine + 0.03 mM nicotinic acid[e] |
| MSR | MS basal medium + 1.7 $\mu$M BAP + 0.2 $\mu$M IBA[d] |
| R5 | MS basal medium + 9.8 $\mu$M IBA + 5.0 nM BAP + 5 $\mu$M GA$_3$[d] |

[a]Difco Laboratories, Detroit, Mich., USA
[b]MS major and minor salts prepared according to Murashige and Skoog (1962), supra. See Table 1b.
[c]B5 vitamins prepared according to a modification of Gamborg, O. L. et al. (1968), "Nutrient requirements of suspension cultures of soybean root cells," Exp. Cell Res. 50: 151–158. See Table 1c.
[d]Sigma Chemical Co., St. Louis, MO., USA. Not necessary for all genotypes.
[e]ICN Nutritional Biochemicals, Cleveland, OH., USA TABLE 1b Minor element stock for MS basal medium (use 40 mls of stock per liter of medium)

| | g/l Stock Solution | g/l in MS Medium |
|---|---|---|
| $H_3BO_3$ | 0.6200 | .02 |
| $MnSO_4.H_2O$ | 1.5640 | .06 |
| (or $MnSO_4$ $4H_2O$) | (2.230) | |
| $ZnSO_4.7H_2O$ | 0.8600 | .03 |
| KI | 0.0830 | .003 |

TABLE 1b-continued

Minor element stock for MS basal medium (use 40 mls of stock per liter of medium)

| | g/l Stock Solution | g/l in MS Medium |
|---|---|---|
| $Na_2MoO_4.2H_2O$ | 0.0250 | .001 |
| $CuSO_4.5H_2O$ | 0.0025 | .0001 |
| (or $CuSO_4$) | (0.0016) | |
| $CoCl_2.6H_2O$ | 0.0025 | .0001 |

TABLE 1c

Stock Solution: B5 vitamins (Use 10 ml of the stock per liter of media)

| | mg/100 ml |
|---|---|
| Nicotinic Acid | 10 |
| Thiamine HCl | 100 |
| Pyridoxine HCl | 10 |
| Myo-inositol | 1 gm |

TABLE 2

Hoaglands - Micronutrient Stock

| | g/l |
|---|---|
| KCl | 3.728 |
| $H_3BO_3$ | 1.546 |
| $MnSO_4.7H_2O$ | 0.846 |
| $ZnSO_4.7H_2O$ | 0.575 |
| $CuSO_4.5H_2O$ | 0.125 |
| $(NH_4)_6Mo_7O_{24}.4H_2O$ | 0.0184 |

Many normal, green plants were transplanted to the greenhouse after rooting had occurred on the MS medium without growth regulators. When this transfer was done directly to the soil mixture the rate of survival was very low and the plants usually remained small. Plants rarely produced more than about 5 seeds, however when these plants were first grown on liquid Hoagland's solution, as described above, and then transplanted to the soil mixture, the survival rate and growth of the plants were greatly enhanced and were nearly normal, except for a few small plants which produced only two or three seeds. All green plants thus obtained, when grown in the greenhouse or the field, were fertile, and bore 10–100 seeds, and plants grown from tneir seeds ($R_1$) developed normally.

After 8d the plants were transplanted to a 1:1:1 peat moss:vermiculite:soil (by vol.) mixture or to the field. The plants were fertilized with a special fertilizer solution made with 7.5 g/l Peters 20:10:20 fertilizer, a product of Peter's Fertilizer Products, W. R. Grace Co., of Fogelsville, Pa. In accordance with D. L. Eskew, et al. (1983), "Nickel: An Essential Micronutrient for Legumes and Possibly All Higher Plants," Science 222: 621–623, nickel has been found to be an essential microelement for legumes. Accordingly a micro-element stock solution as shown in Table 3 was prepared for addition to the fertilizer solution. The fertilizer solution also contains 1 mM $MgSO_4$, and 10 ppm, FeEDTA. The micronutrient stock solution is added to the 20:10:20 fertilizer in the amount of 7.5 ml/l. The solution is then diluted 1:10–1:20 and an amount of 50–100 ml is used for each plant at a frequency of 1 per day.

For histological studies the organogenic calli were fixed by immersing them in fomalin:glacial acetic acid:alcohol (FAA, 2:1:10+6 parts of water, by vol.) for 24 h. Following dehydration in tertiary butanol the material was infiltrated and embedded in commercial paraplast (Monoject Scientific, St. Louis, Mo., USA) in a hot-air oven at 55° C. Microtome sections were cut (10 μm in thickness) and the ribbons were attached to glass slides using Haupt's solution (Johansen, D. A. (1940), Plant Microtechnique. McGraw-Hill Publ., New York, London at 523). The slides were rinsed with xylene to remove the paraplast, and then stained sequentially in safranin 0 dissolved in 50% alcohol for 12 h and fast green (Sigma Chemical Co., St. Louis, Mo., USA) dissolved in 95% alcohol 20-50 s.

TABLE 3

| Fertilizer Micro-elements | |
|---|---|
| 6.25 μM $H_3BO_3$ | 38.65 mg/l |
| 1.0 μM $MnSO_4.H_2O$ | 169.0 |
| 2.0 μM $ZnSO_4.7H_2O$ | 575 |
| 0.5 μM $CuSO_4.5H_2O$ | 123 |
| 0.5 μM $(NH_4)_2MoO_4$ | 98 |
| 0.01 μM $CoSO_4.H_2O$ | 1.78 |
| 0.2 μM $NiSO_4.6H_2O$ | 52.6 |
| Add 5 ml/l conc. $H_2SO_4$ | |

The fifty-four soybean genotypes used in this study included both high shoot producers and low shoot producers identified in a multiple-shoot-forming assay performed with seedlings using some of the soybean germplasm (Barwale et al. (1986), Theor. Appl. Genet., supra). In this assay, shoots were counted at the cotyledonary node. The genotypes were chosen to include much of the variation seen in the collection, including seed color, flower color, maturity time, source of seed, and disease sensitivity and resistance.

All cultures were initiated from immature embryos at different developmental stages, with lengths from 0.5 to 10 mm.

Organogenic callus cultures were obtained from the immature soybean embryos grown on the OR medium with a high 6-benzylaminopurine (BAP) concentration (13.3 μM), 0.2 μM NAA and four to five times the concentration of minor elements in the standard MS medium (Table 5). The most critical factor was the BAP concentration as lower concentrations (3.3 and 6.6 μM) produced low numbers of organogenic cultures (Table 6). A reduced level of minor elements also reduced the response. When each minor element was individually tested at the higher concentration, the other elements being held at the normal (1×) level, only lower levels of molybdate or iron seemed to reduce the response. Thus, no particular minor element seems to be clearly controlling this response. However, the best organogenic callus growth was obtained only when all the minor elements were present at the high concentration. Preliminary experiments showed that embryos 5-6 mm long gave cultures with maximum organogenic capacity; in some genotypes, including cv Williams 82, this was as high as 100% (Table 4).

TABLE 4

Influence of embryo size on organogenesis in callus cultures from immature soybean embryos. Observations were taken four weeks after the cultures were initiated, using cv. Williams 82 on OR with 40 embryos per treatment

| Size (mm) | Organogenesis (%)[a] |
|---|---|
| 1.5 | 0 |
| 2.0 | 0 |
| 3.0 | 21 |
| 4.0 | 53 |
| 5.0-6.0 | 100 |
| 6.0-7.0 | 10 |

TABLE 4-continued

Influence of embryo size on organogenesis in callus cultures from immature soybean embryos. Observations were taken four weeks after the cultures were initiated, using cv. Williams 82 on OR with 40 embryos per treatment

| Size (mm) | Organogenesis (%)[a] |
|---|---|
| 8.0 or larger | — |

[a]Percent of immature embryos plated which formed organogenic cultures

TABLE 5

Effect of higher concentrations of MS minor elements on organogenesis in callus cultures from immature soybean embryos. Observations were taken four weeks after the cultures were initiated, using cv. Williams 82 with 40 embryos per treatment on MS medium with 13.3 μM BAP. The minor elements are $H_3BO_3$, $MnSO_4$, KI, $Na_2MoO_4.2H_2O$, $CuSO_4.5H_2O$ and $CoCl_2.6H_2O$.

| Relative concentration of minor elements | Organogenesis (%)[a] |
|---|---|
| 1 | 80[b] |
| 2 | 75[b] |
| 3 | 60 |
| 4 | 54 |
| 5 | 62 |

[a]Percent of immature embryos plated which formed organogenic cultures
[b]Embryo germination rather than organogenic callus formation

TABLE 6

Effect of BAP concentration of organogenesis in callus cultures from immature soybean embryos. Observations were taken four weeks after the cultures were initiated using cv. Williams 82 with 40 embryos per treatment on MS medium with four times the minor element concentration

| BAP (μM) | Organogenesis (%)[a] |
|---|---|
| 3.3 | 11 |
| 6.6 | 9 |
| 9.9 | 90 |
| 13.3 | 80 |

[a]Percent of immature embryos plated which formed organogenic cultures

Histological studies confirmed the organogenic nature of these cultures. Several shoot meristems were seen. These meristems were not always seen in the same plane as would be the case in a mere proliferation of pre-existing meristems. The observations noted would be typical of de novo initiation of meristemic sites from de-differentiated tissue.

The organogenic cultures were started in the dark. Light induced germination of the original immature zygotic embryo whereas callus obtained in darkness formed shoots either directly, or became organogenic later on. While initial organogenesis (shoot initiation) requires darkness, further growth needs light. After initiation of cultures for four weeks on OR medium, the cultures were placed in light on the proliferation medium, MSR or R5, where they grew very rapidly and needed to be transferred to fresh medium every two to three weeks where more and more shoots are produced. At the high BAP concentration (13.3 μM), cultures formed friable non-organogenic callus after four months. Once shoot regeneration had been initiated, there was no further need for the high concentration of BAP and minor elements in the medium for further proliferation and maintenance of the organogenic cultures. After the shoots had reached about 1 cm in height on MSR or R5 medium, they could be transferred to MS medium without growth regulators to induce root formation, and then were transplanted to the hydroponic medium and then to the greenhouse and grown to maturity.

The organogenic cultures were maintained on MSR or R5 medium for over 18 months and still retained the organogenic capacity and were capable of reproducing plants. With this method, from 10 to 40 plants could be regenerated upon every transfer as each callus could be subdivided into four to six other pieces which proliferated to give additional plants.

With the foregoing methods it is possible to obtain up to 100% plant regeneration via organogenic pathways from immature soybean embryos. This system was successful with all the genotypes tested with only small differences in the percent regeneration. Thus, the genotype differences such as maturity group, seed coat color, etc., did not influence plant regeneration to any substantial degree. There was also no clear correlation of plant regeneration ability with the number of shoots formed at the cotyledonary node.

Example 2: Somaclonal Variation

To determine if plants regenerated from organogenic soybean cultures and progeny of these plants showed spontaneous variation, $R_0$, $R_1$, $R_2$, and $R_3$ plants were examined for morphologically observable qualitative variants.

Soybean (*Glycine max* L. Merr.) seeds of A3127, Adams, Capitol, CN210 Earlyana, PI36.653, PI361.063, PI404.155A and Williams 82 were obtained from the Regional Soybean Germplasm Collection, University of Illinois, Urbana, Ill. Embryogenic and organogenic cultures were initiated from immature embryos and maintained as described in Example 1, and U. B. Barwale, et al. (1986) Planta supra, incorporated herein by reference. Selfed seeds from these plants were planted in the field or sent to a winter nursery in Puerto Rico. Selfed seeds of $R_0$ plants made up one $R_1$ family and each $R_1$ plant made up a new $R_2$ family. No visual observations were taken of the families grown in Puerto Rico but the $R_1$, $R_2$, and $R_3$ families grown in Urbana, Ill. were evaluated extensively for qualitative variants. Twelve seeds of each family were planted in 1.2 meter long rows (0.8 meter space between rows). Control seeds (selfed seeds of plants which did not go through a tissue culture cycle) were also planted for comparison. Evaluations were made for traits such as leaf number; leaf morphology; chlorophyll deficiency; height of the plants; flower color; sterility; multiple branching and shooting; growth habit; pubescence and maturity throughout the growing season. Two hundred sixty three $R_0$ plants produced 263 $R_1$ families of which 153 have been examined in more than one generation. Only $R_1$ families producing more than 12 seeds were grown. Individual $R_1$ plants resulted in the $R_2$ families for the next generation. All the evaluations were done simultaneously for all generations using bulked seeds advanced in Puerto Rico. A total of 66 $R_2$ families (5578 $R_2$ plants) and 548 $R_3$ families (13415 $R_3$ plants) were grown and evaluated visually in this study.

Variant phenotypes were observed in $R_1$, $R_2$ and $R_3$ generations, including chlorophyll deficiency, complete or partial sterility, wrinkled leaf morphology, twin seeds, abnormal leaf morphology, abnormal leaf number, dwarf growth habit and multiple shoots.

Non-lethal chlorophyll deficiency was noted in both $R_2$ and $R_3$ generations of several A3127 families. All leaves of these plants were chlorophyll-deficient and growth was less vigorous than that of control plants. In bulked seed of one family, 2.7% of $R_2$ plants and 7.1% of $R_3$ plants segregated for this trait (Table 7). The segregation ratio in the $R_3$ generation fit a 3:1 model for a recessive, single gene trait indicating the stable inheritance of this trait over generations. Out of 1908 control plants, two showed chlorophyll deficiency (0.1% segregation ratio), eliminating the possibility that this phenotype could be due to environmental factors. Because this trait is stably inherited, the possibility that disease may have resulted in this phenotype is small. Complete sterility was seen in CN210 in the $R_2$ generation. The segregation ratio of 15.6% (Table 7) fits a 3:1 model as determined by Chi-square values. This data suggests a stable inheritance of sterility from the $R_1$ to the $R_2$ generation. Control plants did not exhibit this trait.

The wrinkled leaf type was seen in the $R_3$ generation, 35% of the plants in one family segregated for this phenotype (Table 7). The $R_2$ seeds grown of the same family show very little variation in leaf morphology.

The above mentioned traits indicate that some of the variation seen is stably inherited and appears to be due to genetic changes during the tissue culture process. In three other instances, one phenotype was seen only in the $R_1$ generation (Table 7). Some plants developed twin seeds; but not all seeds on these plants were twin. Abnormal leaf morphology and leaf number were seen as random events. Not all trifoliates on plants showed these phenotypes. The maximum number of trifoliates exhibiting these phenotypes was three. Plants showing dwarf growth habit appeared to be normal in other respects, however the genetics of this trait could not be determined by segregation ratio (Table 7). No differences in flower color were seen. Multiple shoots also appeared as a random event.

For twin seeds, dwarf growth habit, abnormal leaf morphology, leaf number, and multiple shoots (Table 7), current segregation data make it difficult to determine the genetics of these traits. Except for three $R_1$ variants no other variation was seen in this generation (Table 8). However, a high number of $R_2$ and $R_3$ families expressed variant phenotypes.

The frequency of variant phenotypes was calculated by dividing the total number of different qualitative variant phenotypes seen in $R_1$ families of a particular genotype by the total number of $R_1$ families sampled from that same line. This method of calculating the frequency is similar to that of S. Edallo et al. (1981) "Chromosomal variation and frequency of spontaneous mutation associated with in vitro culture and plant regeneration in Maize," Maydica 26: 39–56; and T. B. Rice (1982) "Tissue culture induced genetic variation in regenerated maize inbreds," In: *Proceedings of the Thirty-seventh Annual Corn and Sorghum Industry Research Conference,* American Seed Trade Association, Washington, D.C., pp 148–162. The frequencies ranged from 0–4 per $R_0$ plant (Table 9). The low frequency for A3127 and Williams 82 may be misleading because similar phenotypes were counted once although they may have been similar but independent events; also a large number of $R_1$ families were sampled from these two genotypes. Similar phenotypes could not be counted as separate events since records of the embryo sources were not kept. Thus the origin of each $R_0$ plant could not be determined. Table 10 shows possible mutation frequencies only for 153 $R_1$ families of the total 263 $R_1$ families. The $R_2$ and $R_3$ generations of the remaining 110 $R_1$ families have not been studied.

Plant progeny derived from both embryogenic and organogenic cultures of Williams 82 were examined. Table 9 shows variation seen in the $R_1$ and $R_2$ generation of families derived from both culture systems. One $R_1$ family and 12 $R_2$ families of that $R_1$ family were examined in each culture system. Variants seen in both the systems were similar with a higher frequency of chlorophyll deficiency in embryogenic culture derived plants. Other phenotypes had similar segregation ratios (Table 9). Three sectoral albinos were also seen in $R_0$ plants from embryogenic cultures. These could not be grown to maturity and no seed were obtained.

TABLE 7

Variant phenotypes observed in $R_2$ and $R_3$ families derived from organogenic callus cultures of different genotypes.

| Soybean genotype | Variant phenotype | Number of variants | Total Number of plants | Segregation ratio (%)[a] |
|---|---|---|---|---|
| A3127 | Twin seeds | 2 | 62 | 3.2 |
|  | Dwarf growth | 2 | 30 | 6.6 |
|  | Abnormal leaf morphology | 2 | 26 | 7.7 |
|  | Abnormal leaf number | 1 | 27 | 3.7 |
|  | Wrinkled leaf | 7 | 20 | 35.0* |
|  | Chlorophyll deficiency | 1 | 14 | 7.1* |
| PI36.653 | Multiple shoots | 1 | 25 | 4.0 |
| CN210 | Sterility | 8 | 51 | 15.6* |
| Control |  |  |  |  |
| A3127 | Chlorophyll deficiency | 2 | 1908 | 0.1 |
|  | Dwarf growth | 1 | 1908 | 0.1 |
| CN210 | — | 0 | 140 | 0.0 |
| PI36.653 | Chlorophyll deficiency | 1 | 157 | 0.6 |

[a]Frequency of variant phenotypes within each $R_2$ or $R_3$ family expressing the trait
*Chi-square values fit a 3:1 model at a greater than 0.05 probability level.

TABLE 8

Number of families in different generations showing variant phenotypes.

| Regenerated plant generation | Variant phenotype | Number of families expressing variation |
|---|---|---|
| $R_0$ | Chimeral albino | 3 |
| $R_1$[a] | Chlorophyll deficiency | 1 |
|  | Abnormal leaf morphology | 1 |
|  | Wrinkled leaf type | 1 |
| $R_2$[b] | Chlorophyll deficiency | 11 |
|  | Abnormal leaf morphology | 3 |
|  | Different leaf number | 4 |
|  | Dwarf growth habit | 1 |
| $R_3$[c] | Chlorophyll deficiency | 29 |
|  | Abnormal leaf morphology | 18 |
|  | Different leaf number | 21 |
|  | Dwarf growth habit | 4 |
|  | Wrinkled leaf type | 5 |

[a]200 $R_1$ families examined for variant phenotypes
[b]66 $R_2$ families examined for variant phenotypes
[c]548 $R_3$ families examined for variant phenotypes

TABLE 9

Variant phenotypes observed in $R_1$ and $R_2$ families derived from embryogenic and organogenic callus cultures of Williams 82

| Generation | Variant phenotype | Total Number | Variant number | Segregation ratio (%)[a] |
|---|---|---|---|---|
|  | Embryogenesis |  |  |  |
| $R_2$ | Chlorophyll deficiency | 21 | 6 | 28.5 |
|  | Abnormal leaf morphology | 26 | 1 | 3.8 |
|  | Organogenesis |  |  |  |
| $R_2$ | Chlorophyll deficiency | 25 | 1 | 4.0 |
|  | Abnormal leaf morphology | 31 | 1 | 3.2 |
|  | Abnormal leaf | 30 | 1 | 3.3 |

TABLE 9-continued

Variant phenotypes observed in $R_1$ and $R_2$ families derived from embryogenic and organogenic callus cultures of Williams 82

| Generation | Variant phenotype | Total Number | Variant number | Segregation ratio (%)[a] |
|---|---|---|---|---|
| number |  |  |  |  |

[a]Frequency of variant phenotype within each $R_2$ family expressing that trait.

TABLE 10

Frequency of visible variation in $R_1$ families examined from the nine soybean genotypes used to study somaclonal variation[a]

| Soybean genotype | Number of $R_1$ families[b] | Frequency of mutant phenotype per $R_0$ plants |
|---|---|---|
| A3127 | 76 | 0.11 |
| Adams | 3 | 1.33 |
| Capitol | 1 | 4.00 |
| CN210 | 4 | 1.00 |
| Earlyana | 1 | 1.00 |
| PI36.653 | 15 | 0.53 |
| PI361.063 | 1 | 2.00 |
| PI404.155A | 5 | 1.60 |
| Williams 82 | 47 | 0.11 |

[a]Plants were regenerated from several embryos for a genotype. The time in culture prior to regeneration ranged from 60–350 d.
[b]Number of regenerated plants which set more than 12 seeds
[c]In a given line, the total number of mutant phenotypes seen in all $R_1$ families is divided by the total number of $R_1$ families; identical mutant phenotypes in two or more $R_1$ families of the same genotype is counted as a single mutation event.

Example 3: Disease Resistance

Organogenic and embryogenic callus as described in Example 1 were grown in the presence of a culture filtrate of *Phialophora gregata,* the causative organism for brown stem rot, at concentrations of 1:4 (v/v-filtrate:medium). Seven genotypes were tested as follows: BSR-201, Century, PZ.437.833, Corsoy, A3127, Williams-82, and PI84946-2. Genotypes BSR-201, PZ.437.833 and PZ84946-2 are resistant to brown stem rot (Sebastian, S. A. et al. (1985) J. Hered. 76: 194; Sebastian, S. A. et al. (1985) Crop Sci. 25: 753; Gray, L. E. et al., eds. (1985) *World Soybean Research Conf. III Proceedings,* Westview Press, Boulder, Colo., pp. 59814 601). Friable organogenic and embryogenic callus from the resistant genotypes were not sensitive to the filtrate while the same type calli from the sensitive genotypes were killed by the filtrate. Cultures of the sensitive genotypes were grown in the presence of 1:4 (v/v) (concentration) of the culture filtrate, which was sublethal, and after 30–40 days, cultures exhibiting improved growth were selected for regeneration into disease resistant fertile plants.

Example 4: Herbicide Resistance

Separate organogenic calli as described in Example 1 of genotypes A3127 and Williams 82 were grown in the presence of both toxic and sublethal levels of glyphosate (a non-selective herbicide), paraquat, and atrazine. The concentrations used were as follows: 25 to 200 $\mu$M glyphosate, 5 to 25 $\mu$M paraquat, and 10 to 100 $\mu$M atrazine.

Cultures growing well in the presence of high levels of these substances are selected for regeneration into fertile plants which are resistant to the various herbicides. Paraquat-tolerant cultures are further tested to determine resistant to a number of disease organisms, and diseases linked to paraquat tolerance are identified.

Example 5: Stress Resistance

Separate organogenic calli as described in Example 1 of genotypes A3127 and Williams 82 and were grown in the presence of 40° C. heat and 4° C. cold for varying periods of time. Calli surviving the treatment are tested for proline enhancement, and suitable cultures are selected for regeneration to form stress-resistant, fertile plants.

Example 6: Resistance to Adverse Soil Conditions

Separate organogenic calli as described in Example 1, of genotypes A3127 were grown in the presence of concentrations of 0.001 to 0.3 mM of Cd at pH about 5.7; 0.01–0.6 mM Cu, 0.001–3.0 mM Zn or 0.001–3.0 mM Pb, with Cu, Zn and Pb being about 4–4.2 pH on the growing medium; or 0.1%–10% NaCl. Cultures showing improved growth are selected for regeneration into fertile plants exhibiting resistance to the various adverse soil conditions.

Example 7: Enhanced Amino Acid Over-Production

Separate organogenic cultures as described in Example 1 of genotypes A3127 and Williams 82 were grown in the presence of the toxic analogs to the amino acids at the concentrations shown in Table 11 for 4–8 weeks.

TABLE 11

| Amino Acid Over-Production | | |
|---|---|---|
| Amino Acid | Toxic Analog | Concentration |
| Proline | Hydroxyproline | 0.2–1.2 mM |
|  | Azetidine-z-carboxylate | 0.01–0.03 mM |
| Methionine | Ethionine | 0.01–0.3 mM |
| Tryptophan | 5-Methyltryptophan | 0.01–0.3 mM |
| Phenylalanine | P-fluorophenylalanine | 0.01–3 mM |

Cultures growing well in the presence of the toxic analogs are selected for regeneration into fertile plants with enhanced levels of the amino acid for which selection by the toxic analog was used. Cultures selected with P-fluorophenylanine are further tested for polyphenolic overproduction, and the positives are further tested for various insect and disease resistances. Those showing such resistances are regenerated into fertile plants having the tested-for resistances.

We claim:

1. A method for the production of an organogenic tissue culture comprising cells of *Glycine max* comprising culturing an immature embryo of *Glycine max* to form an organogenic callus culture on a medium comprising BAP at a concentration between about 10 $\mu$M and about 15 $\mu$M and minor elements at a concentration between about four and about six times normal concentration of the micronutrients of MS medium such that germination of the embryo is prevented and organogenic shoot production is promoted.

2. The method of claim 1 wherein the immature embryo is between about 4 and about 6 mm long.

3. The method of claim 1 wherein shoot(s) generated on said medium are regenerated to a whole plant.

4. The method of claim 3 wherein said whole plant comprises a genetically stable mutation induced by somaclonal variation.

5. The method of claim 4 wherein the genetically stable mutation confers a phenotype selected from the group consisting of male sterility, twin seeds, amino acid overproduction, disease resistance, herbicide resistance, stress resistance, heat and cold resistance, ability to tolerate toxic soil conditions, and early maturation.

6. The process of claim 4 wherein the somaclonal variation is induced by applying selection pressure to the tissue culture.

7. The method of claim 3 wherein rooted plantlets regenerated from said tissue culture are placed in a hydroponic medium for further maturation, then in a medium comprising soil.

8. The method of claim 7 wherein said hydroponic medium comprises Hoagland's solution diluted to about 0.25 strength and modified to comprise micronutrients comprising KCl, $H_3BO_3$, $MnSO_4$, $ZnSO_4$, $CuSO_4$, and $(NH_4)_6Mo_7O_{24}$.

9. The method of claim 8 wherein said whole plant is capable of bearing at least about 10 seed per plant.

10. A method for producing a plant of *Glycine max* comprising a heritable characteristic produced by somaclonal variation, said method comprising:
continuously maintaining a tissue culture comprising cells derived from an immature embryo of *Glycine max* on an organogenic culture medium comprising BAP at a concentration between about 10 $\mu$M and about 15 $\mu$M and between about four and about six times normal concentration of the micronutrients of MS medium for a time sufficient to allow somaclonal variation in the genetic material of said cells, regenerating whole plants from said tissue culture, obtaining progeny of said whole plants, observing the desired characteristic in at least two generations of said plants and their progeny, and selecting a progeny plant displaying the desired characteristic.

11. The method of claim 10 wherein the desired characteristic is selected from the group consisting of male sterility, twin seeds, amino acid overproduction, disease resistance, herbicide resistance, stress resistance, heat and cold resistance, ability to tolerate toxic soil conditions, and early maturation.

* * * * *

UNITED STATES PATENT AND TRADEMARK OFFICE
CERTIFICATE OF CORRECTION

PATENT NO. : 4,857,465　　　　　　　　　　　　　　　　Page 1 of 2

DATED : August 15, 1989

INVENTOR(S) : Barwale, Usha B. and Widholm, Jack M.

It is certified that error appears in the above-identified patent and that said Letters Patent is hereby corrected as shown below:

On the first page of the patent after "[73] Assignee: Lubrizol Genetics, Inc., Wickliffe, Ohio" please add --and The Board of Trustees of the University of Illinois, Champaign, Illinois--. On the first page of the patent, column 2, line 9, please rewrite "Tuss." as --Tiss.--. At column 1, line 22, please rewrite "transformtion" as --transformation--. At column 1, line 45, please rewrite "wHere" as --where--. At column 1, line 62, please rewrite " max", " as --max,"--. At column 2, line 34, please rewrite "$\mu$MBA." as --$\mu$M BA.--. At column 3, line 17, please rewrite "et al., in" as --et al., (1977) in--. At column 3, line 19, please delete "(1977)". At column 4, line 21, please delete "(54)". At column 4, line 58, please rewrite "maybe" as --may be--. At column 5, line 32, please rewrite "axially" as --axillary--. At column 6, line 52, please rewrite "$\mu$M protons" as --$\mu$mol photons--. At column 7, line 4, please rewrite "347." as --347).--. At column 7, line 31, please rewrite "10 about" as --10 to about--. At column 8, line 48, please rewrite "supra." as --supra).--. At column 9, line 1, please rewrite "KAlamazoo," as --Kalamazoo,--. At column 9, line 5, please rewrite "self-sterilized" as --surface-sterilized--. At column 10, first line of TABLE 2, please rewrite "Hoaglands" as --Hoagland's--. At column 10, line 45, please rewrite "tneir" as --their--. At column 10, line 65, please rewrite "fomalin:glacial" as --formalin:glacial--. At column 14, line 11, please rewrite "This data suggests" as --These data suggest--.

UNITED STATES PATENT AND TRADEMARK OFFICE
CERTIFICATE OF CORRECTION

PATENT NO. : 4,857,465

DATED : August 15, 1989

INVENTOR(S) : Barwale, Usha B. et al.,

It is certified that error appears in the above-identified patent and that said Letters Patent is hereby corrected as shown below:

At column 14, line 23, please rewrite "twin." as --twins.--
(2nd occurrence)

Signed and Sealed this

Twenty-third Day of October, 1990

Attest:

HARRY F. MANBECK, JR.

Attesting Officer

Commissioner of Patents and Trademarks